United States Patent [19]

Saha

[11] 4,235,243

[45] Nov. 25, 1980

[54] METHOD AND APPARATUS FOR FACILITATING THE NON-INVASIVE, NON-CONTACTING STUDY OF PIEZOELECTRIC MEMBERS

[76] Inventor: Subrata Saha, 178 Highland St., New Haven, Conn. 06511

[21] Appl. No.: 953,640

[22] Filed: Oct. 23, 1978

[51] Int. Cl.³ .............................................. A61B 5/10
[52] U.S. Cl. .................................... 128/740; 128/774; 73/779
[58] Field of Search .............. 128/739, 740, 774, 782, 128/630, 660; 73/573, 574, 584, 779, 763

[56] References Cited

U.S. PATENT DOCUMENTS

| | | | |
|---|---|---|---|
| 2,649,573 | 8/1953 | Goldberg et al. | 128/782 X |
| 3,133,214 | 5/1964 | Lawson et al. | 128/740 |
| 3,302,454 | 2/1967 | Kleesattel | 73/573 |
| 3,323,352 | 6/1967 | Branson | 73/573 |
| 3,477,422 | 11/1969 | Jurist, Jr. et al. | 128/630 |
| 4,048,986 | 9/1977 | Ott | 128/660 X |

FOREIGN PATENT DOCUMENTS 590639  1/1978  U.S.S.R. .................................. 73/574

Primary Examiner—Lee S. Cohen
Attorney, Agent, or Firm—DeLio and Montgomery

[57] ABSTRACT

Method and apparatus for facilitating the non-invasive study of a piezoelectric member, the method including the steps of generating a stress wave in the member at one point and sensing the magnetic field generated in the member at a second point distal to the first point. The apparatus includes an ultrasonic driver for generating the stress wave in the member, and a magnetic field sensor for sensing the generated magnetic field.

15 Claims, 7 Drawing Figures

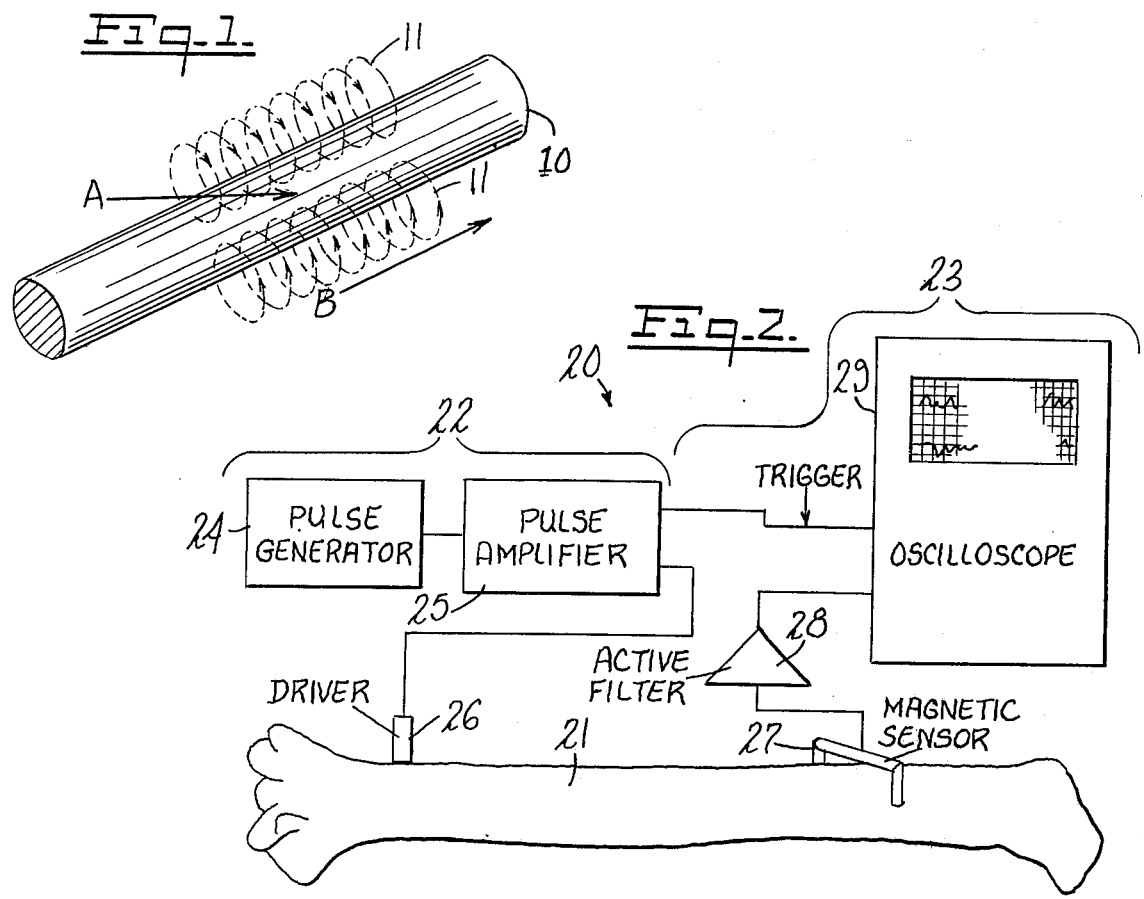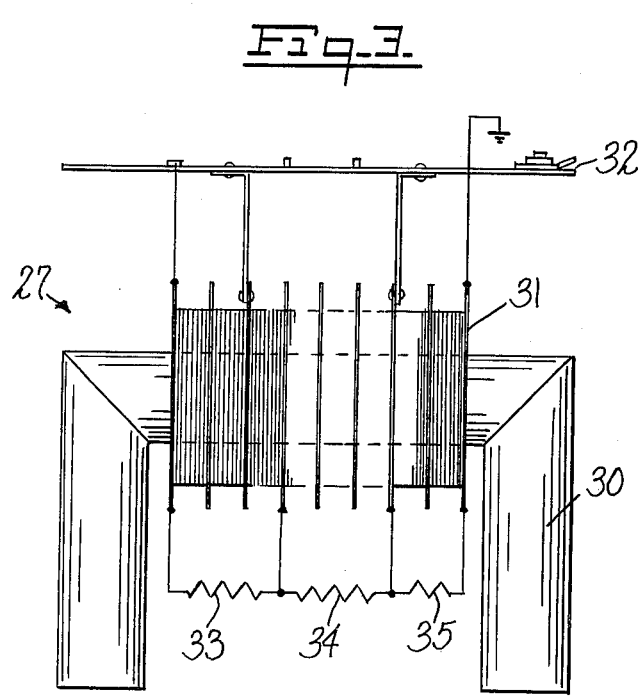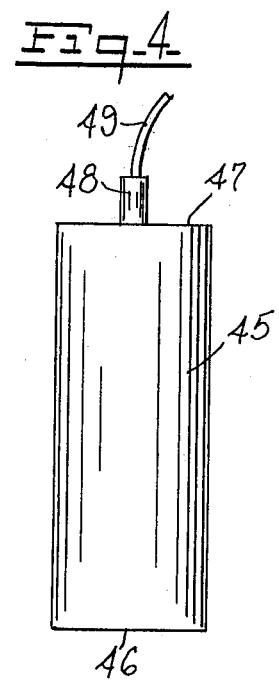

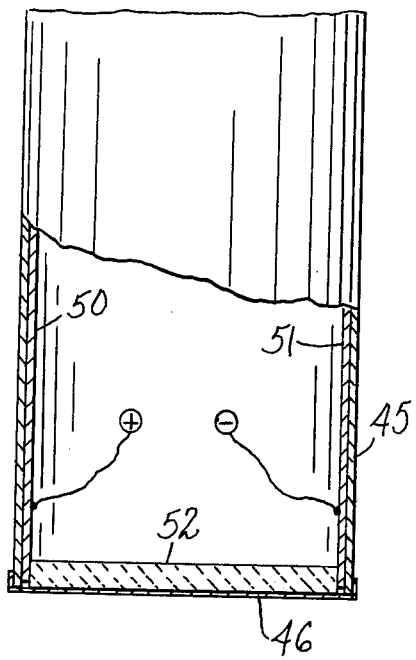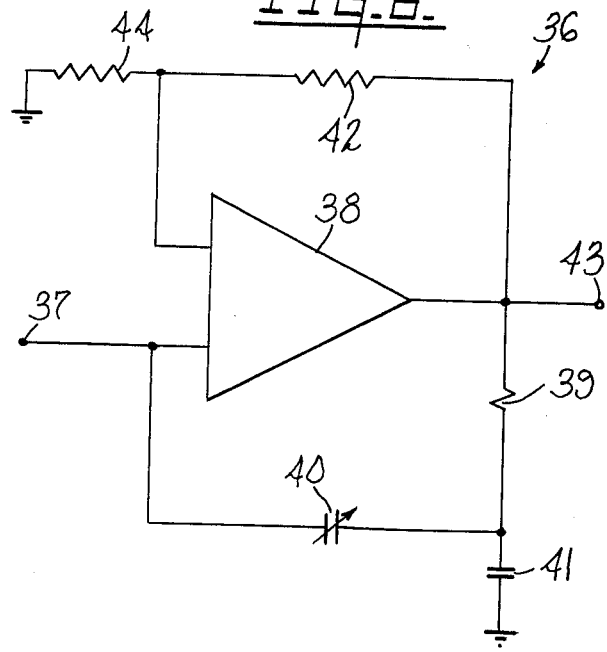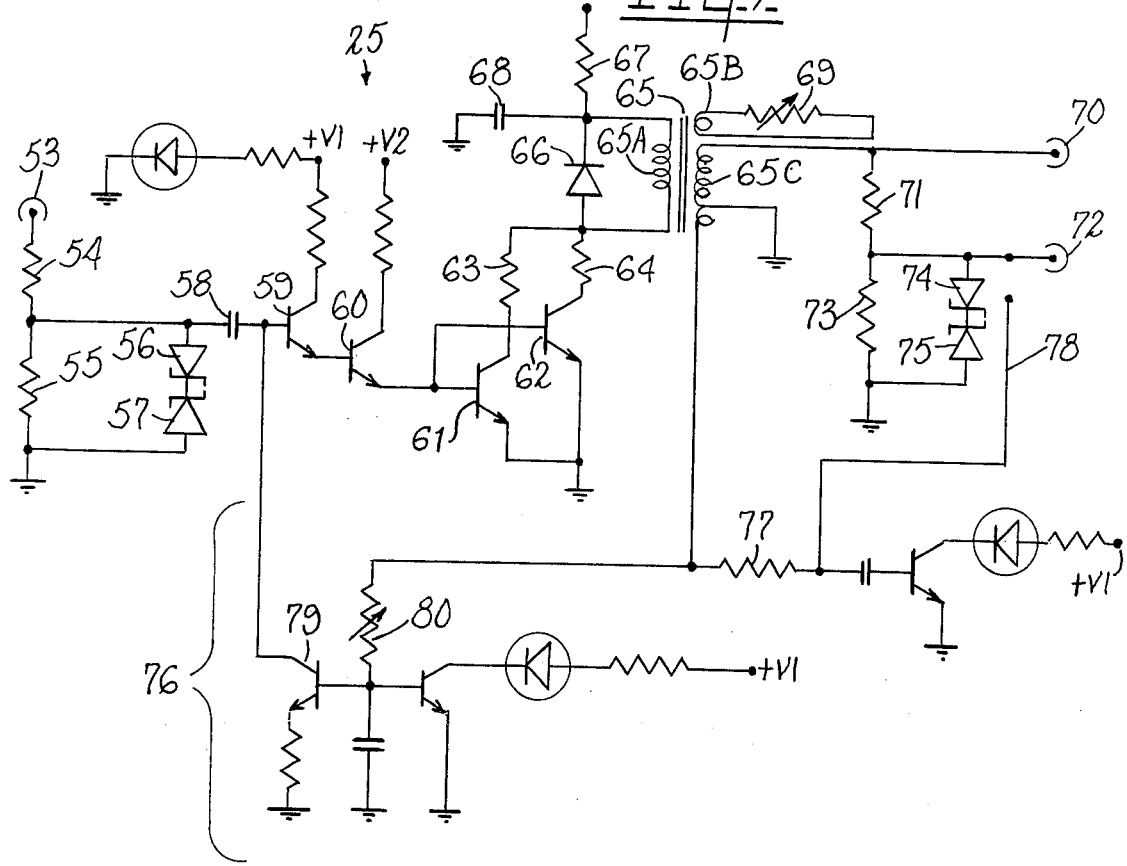

METHOD AND APPARATUS FOR FACILITATING THE NON-INVASIVE, NON-CONTACTING STUDY OF PIEZOELECTRIC MEMBERS

BACKGROUND OF THE INVENTION

1. Field of the Invention

The invention relates generally to methods and apparatus for generating and detecting stress waves in members, and more particularly in members composed of piezoelectric materials.

2. Description of the Prior Art

Certain structural properties, such as mechanical integrity, of members have been studied by ultrasonic techniques. An ultrasonic signal applied to a member generates a stress wave in a structure. Certain characteristics of the detected stress waves, such as relative amplitude, phase, transmission co-efficient, and so forth, may indicate characteristics of the member. Stress wave techniques, which can be non-invasive, are often preferable to invasive techniques, as they avoid destruction of the member under study.

Stress wave techniques are particularly useful in studying certain mechanical properties of bones. Analysis of stress waves can be used to indicate, for example, the amount of healing of a bone fracture, and can also be used to detect the onset and progression of diseases such as osteoporosis long before they can be sensed by standard radiographical techniques.

In studying bone structures, a major drawback to the use of stress wave or vibration techniques is the soft tissue surrounding the bone. Prior art techniques include impedance methods and vibration methods in which the response was measured by pressing accelerometers on the skin above the bone. However, the characteristics of these measurements were significantly affected by the thickness and quality of soft tissue between the accelerometer and bone, as well as by the amount of preload force with which the accelerometer was pressed on the soft tissue. This suggests that in these methods the variations in the quantity and quality of soft tissue from patient to patient constitute a complicating variable which cannot be easily evaluated. It is therefore desirable to provide a method and apparatus for generating stress waves in the bone and for detecting the stress waves which is independent of the mechanical properties of the soft tissue. Prior art techniques included attempts to vibrate the whole bone, which yielded inconclusive results. Other prior art techniques involved using a pin, such as traction pins used in management of some fractures, embedded in the bone at the detector location. The pin vibrates in response to stress waves induced in the bone at that location. This vibration would be independent of the soft tissue effects; however, this approach can be used only for patients having traction pins in the bone. The use of traction pins is an invasive technique, and non-invasive techniques are strongly preferred in this area.

In some materials, such as bone, when the material is mechanically stressed, a magnetic field is generated in response to, and proportional to, the applied stress. An applied stress is propagated as a stress wave through a member in a manner similar to a sound wave propagating therethrough, and, as the stress wave is propagated, the magnetic field follows.

The present invention provides a method and apparatus for studying structural properties of members by providing method and apparatus for generating and detecting stress waves in the members. The method and apparatus facilitate a non-invasive technique for studying certain properties of members such as bones by stress wave techniques which avoids the effects of the soft tissues.

SUMMARY OF THE INVENTION

It is therefore an object of the invention to provide a new and improved method and apparatus for generating and detecting stress waves in members.

It is a further object of the invention to provide a new and improved method and apparatus for generating stress waves in members of piezoelectric material and for detecting the magnetic field generated thereby.

It is a further object to provide a new and improved method and apparatus which facilitates the study of mechanical properties of members of piezoelectric material by generating a stress wave therein and detecting the magnetic field generated thereby.

It is yet another object of the invention to provide a new and improved method and apparatus which facilitate studying the mechanical integrity of piezoelectric material such as a bone structure by generating a stress wave and detecting the magnetic wave generated in the bone structure thereby.

In brief, the invention provides a method and apparatus for generating and detecting a stress wave in a piezoelectric member. The method includes the steps of generating an ultrasonic pulse in an ultrasonic driver pressed against one end of the member under study, sensing the magnetic field generated in the piezoelectric material at the other end of the member, generating an electrical signal in response to the sensed magnetic field, and displaying or otherwise recording the electrical signal. The apparatus includes a pulse generator to generate electrical pulses to drive the ultrasonic driver. The sensing portion of the apparatus includes a magnetic sensor, an active filter for rejecting the 60-cycle interference from the AC power line, and a display or recording device, such as an oscilloscope, to display or record the electrical signals generated in the magnetic sensor.

BRIEF DESCRIPTION OF THE DRAWINGS

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated in the claims.

For a fuller understanding of the invention, reference is had to the following description taken in connection with the accompanying drawings, in which:

FIG. 1 is an isometric view of a piezoelectric rod showing the magnetic field resulting from a stress pulse generated therein;

FIG. 2 is a block diagram of the preferred embodiment according to the invention;

FIG. 3 is a front elevational view of a magnetic sensor according to the invention;

FIG. 4 is a side elevational view of an ultrasonic driver according to the invention;

FIG. 5 is a view partially in section of the lower portion of the ultrasonic driver shown in FIG. 4;

FIG. 6 is a schematic diagram of a preamplifier for use with the magnetic sensor of FIG. 3; and FIG. 7 is a schematic diagram of a pulse amplifier for use in the apparatus shown in FIG. 2.

DETAILED DESCRIPTION OF THE PREFERRED EMBODIMENT

FIG. 1 exemplifies a rod 10 of piezoelectric material. When the rod is stressed in the region A, a magnetic field 11 is generated. The stress in rod 10 generates stress waves in the piezoelectric rod which travel longitudinally through the rod as exemplified by arrow B. The propagating stress waves carry with them the magnetic field induced thereby.

FIG. 2 exemplifies apparatus 20 according to the invention for generating and detecting a stress wave in a member of piezoelectric material exemplified by bone 21. The apparatus includes a stress pulse generating portion 22 and a stress pulse detecting portion 23.

Stress pulse generating portion 22 of apparatus 20 includes a pulse generator 24 which generates an electrical pulse, a pulse amplifier 25 and an ultrasonic driver 26. The pulse amplifier receives the electrical pulse from the pulse generator 24 and amplifies it. Driver 26 receives the pulse from the pulse amplifier 25 and generates a mechanical ultrasonic pulse in response thereto. A particular configuration of ultrasonic driver 26 useful with the invention will be described hereinafter.

A pulse generator 24 useful with the invention is the Tektronix Type 505 pulse generator manufactured and sold by Tektronix Incorporated of Beaverton, Or.

Stress pulse detecting portion 23 includes a magnetic sensor 27 (described hereinafter) an active filter 28 which serves to filter out any 60-cycle AC interference from the power lines, and a display device such as an oscilloscope 29. An oscilloscope is shown by way of example only and not limitation. Other display devices such as chart recorders, or recording devices could also be used with the invention.

FIG. 3 exemplifies a magnetic sensor 27 according to the invention. Magnetic sensor 27 includes a U-shaped ferrite core member 30 and a wire coil 31 wrapped around the cross member of U-shaped member 30. A preamplifier 32 is mounted directly to sensor 27 to reduce the lead length from the coil 31 to the preamplifier as explained hereinafter. The coil is separated into eight sections to minimize capacitance across the coil, and damping resistors 33 through 35 are provided across certain sections of the coil.

It is known that the distributed capacitance between the windings of coil 31 and leakage inductance between the coil and the ferrite core 30 form a resonant circuit. The inductance of the sensor 27 and the input capacitance of the preamplifier 32 also constitute a resonant circuit. These resonances limit the portion of the frequency domain in which the sensor can be used to detect the pulsed stress waves and in effect place an upper bound on the useable sensitivity of the device. These resonances can be extended to higher frequencies, however, by reducing the referenced capacitances. The inter-winding capacitance can be reduced by dividing the windings of coil 31 into segments. The input capacitance of the preamplifier 32 can be reduced by placing the preamplifier as close to the magnetic sensor 27 as possible, to reduce the lead length from coil 31 to preamplifier 32. The damping resistors 33 through 35 are included to reduce the otherwise sharp LC resonance which would otherwise induce excessive ringing to the pulse response of the sensor.

FIG. 6 exemplifies a preamplifier 36 for use with magnetic sensor 27. The preamplifier has been designed to employ feedback to simulate a negative capacitive input so that a portion of the source capacitance of the sensor as well as the preamplifier capacitance is neutralized. The preamplifier includes an input 37 to the inverting terminal of operational amplifier 38. A feedback loop is provided through resistor 39 and variable capacitor 40. A capacitor 41 is connected between the junction between resistor 39 and variable capacitor 40 and ground. Capacitor 41 and resistor 39 reduce the feedback at higher frequencies which tends to increase the stability of preamplifier 36 at the higher frequencies. The preamplifier also includes a resistor 42 between the output 43 and the non-inverting input to operational amplifier 38, and a resistor 44 from the non-inverting input to ground.

FIGS. 4 and 5 exemplify an ultrasonic driver useful with the invention. Driver 26 comprises a cylindrical body 45 having the lower end closed off by a thin metal foil 46. The top of the driver is sealed by a plate 47 that supports a connector 48 which receives lines 49 from the pulse amplifier 25. Inside driver 26, two electrodes 50 and 51 run down opposite sides of body 45 from the top to the bottom. Electrodes 50 and 51 support disc 52 made of a piezoelectric material such as lead-titanate-zirconate ceramic, that vibrates in response to an electrical pulse being applied thereto. Electrode 50 is connected to the positive terminal of connector 48 and electrode 41 is connected to the negative terminal. When an electrical pulse is received at connector 48 the disc 52 is electrically stressed by the signal passing down electrodes 50 and 51 and vibrates ultrasonically. This in turn vibrates foil cover 46.

FIG. 7 exemplifies a pulse amplifier useful with the invention. The pulse amplifier was designed to be compact to minimize the effects of the external magnetic interference. Pulse amplifier 25 comprises an input 53 connected to two resistors 54, 55 in series. Resistor 55 is in turn connected to ground. Across resistor 55 are two zener diodes 56, 57 connected anode to anode. A capacitor 58 is also connected to the junction between resistor 54 and resistor 55. Capacitor 58 is in turn connected to the base of transistor 59, the emittor output of which drives the base of transistor 60. Transistor 60 in turn drives two transistors 61 and 62 which, with their respective collector resistors 63, 64, are driven in parallel to increase the current, and hence power, output. Transistors 61 and 62 together drive the primary winding of transformer 65. A diode 66 is connected in parallel across the primary winding 65A of transformer 65. Diode 66 is reversed biased through resistor 67 to voltage supply V3. A capacitor 68 sends stray signals to ground.

Secondary winding 65B of transformer 65 is connected to a damping resistor 69. Secondary winding 65C of transformer 65 is connected to output 70 and, through resistor 71 and output 72, to trigger the recording or display device. Resistor 71 is also connected to resistor 73 which has zener diodes 74 and 75 connected in series, anode to anode, thereacross.

Secondary winding 65C of transformer 65 is also connected to a current limiting circuit 76. Current limiting circuit 76 provides protection for transistors 59–62 by limiting the current passing through the transistors as the input voltage from the pulse generator is increased.

It comes into play only after a threshold input has been reached.

Secondary winding 65C of transformer 65 is connected to supply an inverted signal to current limiting circuit 76 at one side of resistor 77. The other side of resistor 77 is connected to a line 78 which is capacitively coupled to zener diodes 74 and 75, and which senses a non-inverted signal therefrom. The inverted signal is fed to the base of transistor 79 through variable resistor 80. Variable resistor 80 varies the amount of signal received by transistor 79 from the secondary of transformer 65. The inverted signal varies the collector-emitter impedance of transistor 79 thereby varying the biasing voltage received at the base of transistor 59, lowering it at a higher pulse input level and raising it a lower pulse input level.

The pulse amplifier, in operation, receives a pulse at input 53 which is amplified by transistor 59. Zener diodes 56 and 57 limit the voltage and assist in shaping the pulse. The amplified pulse is then further amplified by transistor 60 and by parallel transistors 61 and 62. The pulse is then fed through transformer 65 to output 70. Output 72 provides a signal to trigger oscilloscope 29.

The current limiting circuit 76 receives an inverted form of the output signal from secondary winding 65B, which inverted signal is fed to transistor 79. Variable resistor 80 serves to vary the input level to transistor 79. Transistor 79, as its collector-emitter impedance is varied in response to the signal applied to its base, varies the base-to-ground impedance, and the bias voltage level, for transistor 59, controlling the operating points of the transistor and hence the current passing therethrough. This also controls the current passing through the other transistors 60–62.

The operation of apparatus 20 will now be described. The region of the member 21 whose properties are to be studied must first be selected. The ultrasonic driver is placed to the structure at one side of the selected region and the magnetic sensor 27 is placed proximate the structure to the other side of the region, such that the region under study lies between the driver 26 and magnetic sensor 27. This is to insure that the sensed stress waves will pass through the region under study. The pulse generator is actuated to supply electrical pulses to pulse amplifier 25. The pulse amplifier amplifies the electrical pulses received from the pulse generator and pulse amplifier. The ultrasonic driver 26 is placed in close mechanical contact with member 21. The pulses from the ultrasonic driver stress the structure and generate stress waves therein. The stress waves propagate through member 21, generating a magnetic field (as shown in FIG. 1) as they travel.

The magnetic sensor 27 senses the magnetic field in the core 30. The magnetic field induced in core member 30 by the propagating stress waves varies with time and an electrical signal is generated in coil 31. The preamplifier 32 amplifies the signal generated in coil 31 by the stress wave. The active filter 28 is provided to filter out any extraneous known sources of interference, the most important of which is the 60 Hz AC line interference. The signal from the active filter is then fed to the oscilloscope 29 which displays the signal from the preamplifier.

The particular magnetic sensor 27 herein described is also by way of example. Any magnetic sensor capable of sensing very small levels of magnetism could be used in performing the method. A U-shaped core member 30 is provided to permit the sensor to sense the magnetic field on opposite sides of member 21. The particular configuration of magnetic sensor 27 is especially useful in studying bones, for example, of extremeties or of other elongated members.

Pulse generators other than that described herein can also be used with apparatus 20. Suitable ultrasonic drivers are also commercially available. The ultrasonic driver must receive the electric pulse from the pulse amplifier and generate an ultrasonic mechanical pulse in response thereto, and must be capable of applying the mechanical ultrasonic pulse to the member under study.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

I claim:

1. A method of facilitating the non-invasive study of a portion of a piezoelectric member comprising the steps of:
   generating a stress wave in said member at one end of the portion under study; and
   sensing the magnetic field generated by said stress wave at the other end of the portion of said member under study.

2. A method as set forth in claim 1 in which said stress wave generating step includes the steps of placing a driver to said member at the one end of the portion under study, said driver being adapted to receive an electrical pulse and generating a mechanical pulse in response thereto, and supplying an electrical pulse to said driver.

3. A method as set forth in claim 1 in which said magnetic field sensing step includes the steps of placing a magnetic sensor to the other end of the portion under study, sensing said magnetic field with the magnetic sensor, and generating an electrical signal in response to the sensed magnetic field.

4. A method of facilitating the non-invasive study of a portion of a bone member comprising the steps of:
   applying a driver to the bone member at one end of the portion under study, said driver being adapted to receive an electrical pulse and generate a mechanical pulse in response thereto;
   supplying an electrical pulse to said driver;
   placing a sensor adapted to sense a magnetic field proximate said bone member at the other end of said portion,
   sensing the magnetic field generated in the bone with the sensor by the pulse supplied by the driver; and
   generating an electrical signal in response to the sensed magnetic field.

5. A method as set forth in either of claims 1 or 4 further comprising the step of displaying the sensed magnetic field as a function of time.

6. A method as set forth in either of claims 1 or 4 further comprising the step of recording the sensed magnetic field as a function of time.

7. Apparatus facilitating the non-invasive study of a portion of a piezoelectric member comprising:
   a generator means for generating electrical pulses;
   a driver means connected to receive the electrical pulses and generate mechanical pulses in response thereto, said driver means being adapted to be placed to the member; and means adapted to be placed proximate the member for sensing the magnetic field generated in the member by the mechanical pulse from the driver means, and for generating an electrical signal in response thereto.

8. Apparatus as set forth in claim 7 in which said driver means comprises an ultrasonic driver including means adapted to vibrate in response to an electrical pulse being applied thereto, and means for connecting said means adapted to vibrate to said electrical pulse generator means.

9. Apparatus as set forth in claim 7 in which said magnetic field sensing means includes a U-shaped core member of magnetizable material, the legs of said member being separated sufficiently to facilitate the sensing means to at least partially encircle said piezoelectric member, and a wire coil around said core member.

10. Apparatus as set forth in claim 7 further comprising means for displaying the electrical signal as a function of time.

11. Apparatus as set forth in claim 7 further comprising means for recording the electrical signal as a function of time.

12. A method for testing the physical properties of a portion of a piezoelectric member comprising:

generating stress waves in said member at one end of the portion of the member, and sensing the magnetic field generated by the stress waves at the other end of the portion of the member.

13. A method for non-invasive testing of an in vivo bone member comprising:

generating stress waves in the bone member at one end of the member, and sensing the magnetic field generated by the stress waves at the other end of the member.

14. The method of claim 12 or 13 wherein sensing the magnetic field comprises:

sensing the magnetic field at an area proximate to the member.

15. The method of claim 12 or 13 wherein generating stress waves comprises applying a mechanical pulse to the member.

* * * * *